United States Patent
Da Mota Martins Gonçalves et al.

(10) Patent No.: US 11,167,013 B2
(45) Date of Patent: Nov. 9, 2021

(54) SUCROSE ACETATE ISOBUTYRATE-BASED COMPOSITIONS, METHODS AND USES THEREOF

(71) Applicant: ASSOCIATION FOR THE ADVANCEMENT OF TISSUE ENGINEERING CELL BASED TECHNOLOGIES & THERAPIES (A4TEC)-ASSOCIAÇÃO, Braga (PT)

(72) Inventors: Cristiana Da Mota Martins Gonçalves, Braga (PT); Simone Dos Santos Silva, Braga (PT); Fátima Raquel Azevedo Maia, Vila Do Conde (PT); Hajer Radhouani, Braga (PT); Joaquim Miguel Antunes Correia De Oliveira, Braga (PT); Rui Luís Gonçalves Dos Reis, Oporto (PT)

(73) Assignee: ASSOCIATION FOR THE ADVANCEMENT OF TISSUE ENGINEERING CELL BASED TECHNOLOGIES & THERAPIES (A4TEC)—ASSOCIAÂO, Braga (PT)

(*) Notice: Subject to any disclaimer, the term of this patent is extended or adjusted under 35 U.S.C. 154(b) by 0 days.

(21) Appl. No.: 16/620,823

(22) PCT Filed: Jun. 11, 2018

(86) PCT No.: PCT/IB2018/054213
§ 371 (c)(1),
(2) Date: Dec. 9, 2019

(87) PCT Pub. No.: WO2018/225050
PCT Pub. Date: Dec. 13, 2018

(65) Prior Publication Data
US 2020/0188486 A1 Jun. 18, 2020

(30) Foreign Application Priority Data
Jun. 9, 2017 (PT) .......................... 110132

(51) Int. Cl.
*A61K 38/25* (2006.01)
*A61K 38/18* (2006.01)
(Continued)

(52) U.S. Cl.
CPC ............ *A61K 38/25* (2013.01); *A61K 38/185* (2013.01); *A61K 38/1808* (2013.01);
(Continued)

(58) Field of Classification Search
CPC ............ A61K 38/1858; A61K 38/1808; A61K 9/0024; A61K 47/34; A61K 47/26;
(Continued)

(56) References Cited

U.S. PATENT DOCUMENTS 5,747,058 A 5/1998 Tipton et al.
5,968,542 A * 10/1999 Tipton .................... A61L 27/54
424/423
(Continued)

FOREIGN PATENT DOCUMENTS

WO 2014032099 3/2014
WO 2014032099 A1 * 3/2014

OTHER PUBLICATIONS

Simone S Silva et al, "Green processing of porous chitin structures for biomedical applications combining ionic liquids and supercritical fluid technology", Acta Biomaterialia, Elsevier, Amsterdam, NL, vol. 7, No. 3, doi:10.1016/J.ACTBIO.2010.09.041, ISSN 1742-7061, (Sep. 30, 2010), pp. 1166-1172.
(Continued)

*Primary Examiner* — Blessing M Fubara
(74) *Attorney, Agent, or Firm* — Leason & Ellis LLP (57) ABSTRACT

The present disclosure relates to a composition for the release of the bioactive substance comprising: sucrose
(Continued)

acetate isobutyrate dissolved in an ionic liquid and an additive selected from the list consisting of: chitin, silk fibroin, cellulose, alginate, chitosan, gellan gum, dextrin, collagen, guar gum, carregeenan, heparin, kefiran, or mixtures thereof. By taking advantage of the properties of an ionic liquid (IL), in particular 1-butyl-imidazolium acetate (BMIMAc), it was possible to achieve a good dissolution of SAIB, which combined with chitin and/or silk, natural polymers, allows the development of the structures with different shape and sizes.

12 Claims, 10 Drawing Sheets

(51) Int. Cl.
```
A61K 45/06      (2006.01)
A61K 47/02      (2006.01)
A61K 47/26      (2006.01)
A61K 47/34      (2017.01)
A61K 47/36      (2006.01)
A61K 47/38      (2006.01)
```
(52) U.S. Cl.
CPC .......... *A61K 38/1858* (2013.01); *A61K 45/06* (2013.01); *A61K 47/02* (2013.01); *A61K 47/26* (2013.01); *A61K 47/34* (2013.01); *A61K 47/36* (2013.01); *A61K 47/38* (2013.01)

(58) Field of Classification Search
CPC ...... A61K 47/38; A61K 38/185; A61K 38/25; A61K 45/06; A61K 47/02; A61K 47/14; A61K 47/42; A61L 27/20; A61L 27/227; A61L 27/505; A61L 27/56; C08L 5/08
See application file for complete search history.

(56) References Cited

U.S. PATENT DOCUMENTS 8,906,476 B2 * 12/2014 Tan ................. B41M 5/5254
428/32.21
2004/0101557 A1 * 5/2004 Gibson ............. A61L 26/0066
424/484
2016/0100578 A1 * 4/2016 Ghandi ............. A61L 29/085
428/532

OTHER PUBLICATIONS

Reynolds RC, "Metabolism and pharmacokinetics of sucrose acetate isobutyrate (SAIB) and sucrose octaisobutyrate (SOIB) in rats, dogs, monkeys or humans: a review", Food and Chemical Toxicology, (1998), vol. 36, No. 2, pp. 95-99.

Cheng T.L. et al., "A sugar-based phase-transitioning delivery system for bone tissue-engineering", Eur Cell Mater, (2013.), vol. 26, pp. 208-221.

FDA U. Part 172—Food additives permitted for direct addition to food for human consumption. § 172.898—Bakers yeast glycan. Code of Federal Regulations (CFR) Title, (2006). 98 pages (p. 98).

Silva SS, Mano JF, Reis RL. Ionic liquids in the processing and chemical modification of chitin and chitosan for biomedical applications. Green Chemistry. 2016. 13 pages.

Al Sagheer F; Al-Sughayer M; Muslim S; Elsabee MZ, "Extraction and characterization of chitin and chitosan from marine sources in Arabian Gulf", Carbohydrate Polymers, (2009), vol. 77, No. 2, doi:doi:10.1016/j.carbpol.2009.01.032, pp. 410-419.

Okumu et al., Sustained delivery of human growth hormone from a novel gel system: SABERTM, Biomaterials, (Nov. 2002) vol. 23, issue 22, pp. 4353-4358.

Lee SH et al., "Chapter 10—Preparation of biopolymer-based materials using ionic liquids for the biomedical application." In Ionic Liquid Applications: Pharmaceuticals, Therapeutics, and Biotechnology, Malhotra, S., Apr. 28, 2010. pp. 116-134 (pp. 115, 118, 122, 124 and 125).

Muzzarelli, R., Biomedical Exploitation of Chitin and Chitosan via Mechano-Chemical Disassembly, Electrospinning, Dissolution in Imidazolium Ionic Liquids, and Supercritical Drying. Marine Drugs, vol. 9, pp. 1510-1533, (Sep. 9, 2011).

International Search Report and Written Opinion dated Oct. 9, 2018, corresponding to International Patent Application No. PCT/IB2018/054213; 9 pages.

* cited by examiner

SUCROSE ACETATE ISOBUTYRATE-BASED COMPOSITIONS, METHODS AND USES THEREOF

CROSS-REFERENCE TO RELATED PATENT APPLICATIONS

This application is a U.S. National Stage Application under 35 U.S.C. § 371 of International Patent Application No. PCT/IB2018/054213, filed Jun. 11, 2018, which claims the benefit of priority to Portuguese Patent Application No. PT 110132 filed Jun. 9, 2017, both of which are hereby incorporated by reference as if set forth in their respective entireties herein.

TECHNICAL FIELD

The present disclosure relates to an innovative technology by green processing sucrose acetate isobutyrate (SAIB) into 2D and 3D-based matrices. By taking advantage of the properties of an ionic liquid (IL), in particular 1-butyl-imidazolium acetate (BMIMAc), it was possible to achieve a good dissolution of SAIB, which combined with chitin, a natural polymer, allows the development of the structures with different shape and sizes.

BACKGROUND

Figure 1:
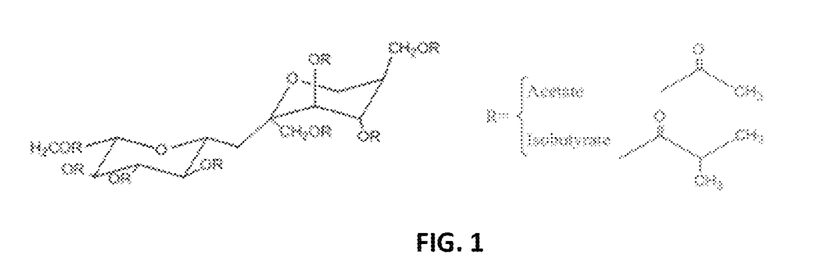
FIG. 1. Sucrose acetate isobutyrate —$C_{40}H_{62}O_{19}$.

Sucrose acetate isobutyrate (SAIB), a synthetic disaccharide (FIG. 1), is a stable liquid composed of mixed acetyl and isobutyl esters of sucrose [1]. It is fully esterified at a ratio of six isobutyrate groups to two acetate groups. SAIB has an average molecular weight of 846.91 g·mol$^{-1}$ and a density of 1.146 g·mL$^{-1}$ at 25° C. This sugar-based ester is non-crystalline, highly lipophilic, water insoluble, showing semisolid material properties and high viscosity (over 100 Pa·s). SAIB can be prepared by controlled esterification of sucrose (food grade) with acetic and isobutyric anhydrides, in the presence of a catalyst. The produced ester can be purified carrying out a filtration and distillation steps.

The addition of small amounts (such as 10-35%) of pharmaceutically acceptable organic solvents (such as ethanol, NMP, DMSO, benzyl alcohol and benzyl benzoate) leads to a significant decrease in viscosity, a final value of about 50-200 mPa·s, similar to the viscosity of a vegetable oil. These formulations could be easily injected through standard needles. Then, when the solvent disperses, the SAIB switch to its highly viscous (semi-solid) properties, creating depots. Moreover, SAIB is biocompatible and biodegradable to natural metabolites and potentially provides a resource for delivery and controlled release of drugs, from the depots created.

SAIB is traditionally and largely used as an emulsifying agent (E444), stabilizer and a direct additive to human diets in the food industry. As an emulsifier, SAIB is used in many countries as a 'weighting' or 'density-adjusting' agent in non-alcoholic carbonated and non-carbonated beverages [1]. SAIB is listed on FDA as "Food additives permitted for direct addition to food for human consumption (Sec. 172.833 Sucrose acetate isobutyrate)" [3] but also on "Indirect food additives: adhesives and components of coatings (Sec. 175.105 Adhesives)". As food addictive it has an allowable daily intake of 20 mg·(kg·day)$^{-1}$ [2].

Beyond its applications in the food and cosmetics industries, it has only been studied and commercially exploited for controlled-release oral and subcutaneous drug delivery. Some of the SAIB related documents (WO9639995) and products (DURECT SABER® Platform) are linked to its capability to change from viscosity extremes and also to its slow rate of drug release.

These facts are disclosed in order to illustrate the technical problem addressed by the present disclosure.

GENERAL DESCRIPTION

The present disclosure relates to a composition for the release of the bioactive substance comprising: sucrose acetate isobutyrate dissolved in an ionic liquid and an additive selected from the list consisting of: chitin, silk fibroin, cellulose, alginate, chitosan, gellan gum, dextrin, collagen, guar gum, carregeenan, heparin, kefiran, or mixtures thereof.

The composition of the present disclosure avoided the use of organic solvents and surprisingly with this composition it is possible obtain scaffolds, membranes, or 3D structures.

The structural features of the produced matrices were evaluated using FTIR, SEM, and XRD. The findings obtained from FTIR analysis confirmed the presence of chitin and SAIB as well the effect of the solvent used for the IL removal. The XRD analysis suggests that the presence of SAIB, aligned with the dissolution action of the IL, contributes to decrease the crystallinity of the scaffolds. Moreover, the cells were able to spread in the SAIB scaffolds, indicating a positive effect.

Chitin is a linear polymer, composed by repeating N-acetylglycosamine units. This polymer can be found in crustacean shells, squid pen, cuticles of insects, and the cell walls of fungi [4]. Chitin has received widespread attention due to its availability, biodegradability and non-toxicity. Despite its availability, the processability of chitin is difficult, due to the presence of strong inter- and intramolecular hydrogen bonds. Recently, progress in the processability of chitin has been achieved by the use of ionic liquids (ILs), which have opened up new ways to process it, not only as hydrogels but also as matrices in different shapes and sizes.

*Bombyx mori* silk fibroin (SF), a fibrous protein that is derived from the silk *Bombyx* cocoon, is composed of 18 short sidechain amino acids that form antiparallel sheets in the spun fibers. SF is considered to be a suitable material for the design of porous matrices with potential advantages in terms of biocompatibility, chemistry versatility, and in vivo minimal inflammatory reaction. Notwithstanding, silk's exceptional biocompatibility as a cell culture on silk-based biomaterials has resulted in the formation of a variety of tissues including cartilage both in vitro and in vivo. ILs are organic salts that contain organic cations as imidazolium, pyridinium pyrrolidinium or ammonium derivatives. Those can be related with organic anions such as $CH_3COO^-$ or inorganic anions such as $Cl^-$, $Br^-$, $I^-$, $BF_4^-$ to design a particular IL. ILs are stable in the liquid form at a temperature below 100° C. The ILs have high ionic conductivity ($10^{-4}$ to $10^{-2}$ S·cm$^{-1}$), non-inflammability and negligible vapor pressure. Furthermore, they exhibit also high thermal (up to 300° C.) and electrochemical stability (4-5.7 V). ILs have low volatility allowing recycling, by evaporation of water or other solvent (e.g. ethanol), and reuse. The application of ionic liquids (ILs) has been motived by unique physic-chemical properties of ILs, enabling the utilization of the ILs-based materials in a broad range of fields namely chemical, pharmaceutical, energy, biotechnology, among others. In the biomedical field, the role of ILs is not only as solvent but also as reaction media for biomacromolecules (e.g. chitin, chitosan, cellulose), as it has been demonstrated in the literature. Therefore, ILs such as 1-buthyl-imidazolium acetate (BMIMAc) and 1-ethyl-3-methylimidazolium chloride (BMIMCl) has been used to create materials including sponges, films, microspheres and aerogels [4]. Moreover, ILs have a key role in chemical reactions, hydrolysis, crosslinking and graft copolymerization towards promoting homogeneous media and thus enhancing the efficiency of the reactions. In this context, ILs emerged as a promising solvent also for SAIB. Since the use of ILs as solvents can promote homogeneous reaction media, crosslinking reactions using genipin, a natural crosslinking agent, could be useful There are no reports in literature suggesting the use of ILs for the dissolution and processing of SAIB. This has never been done before and the trigger motivation for this work was due to the SAIB solubility. In fact, since it is impossible to dissolve SAIB in water, or aqueous solutions, it is being used dissolved in organic solvents, which is not the most appropriate solvent for biological approaches.

The present disclosure explores the potential of SAIB in tissue engineering scaffolding applications and regenerative medicine. The processing of SAIB with ILs was investigated by selecting the best procedure and type of IL. The final scaffolds properties were tuned by blending (e.g. silk fibroin and chitin). The referred process includes the dissolution, molding (gels and membranes) and removal of the IL. The resulting 2D and 3D structures were achieved by means of freeze-drying technique. The obtained films, hydrogels and scaffolds, proposed for an extended range of tissue engineering approaches (such as skin and cartilage regeneration), were extensively characterized. The physicochemical characterization performed comprised microCT, adhesivity, FTIR, XRD, SEM and swelling. The in vitro studies performed covered cytotoxicity evaluation of SAIB scaffolds and biocompatibility analysis of SAIB scaffolds.

The present disclosure relates to a composition for the release of a substance, in particular a bioactive substance, comprising sucrose acetate isobutyrate and an additive selected from chitin, silk fibroin, cellulose, alginate, chitosan, gellan gum, dextrin, collagen, guar gum, carregeenan, heparin, kefiran, or mixtures thereof, in particular wherein the sucrose acetate isobutyrate is dissolved in an ionic liquid.

In an embodiment, the composition may comprise
10-60% (w/V) of sucrose acetate isobutyrate;
40-90% (w/V) of the additive selected from chitin, silk fibroin, cellulose, alginate, chitosan, gellan gum, dextrin, collagen, guar gum, carregeenan, heparin, kefiran, or mixtures thereof.

In an embodiment, the composition may comprise 30-50% (w/V) of sucrose acetate isobutyrate, preferably 35-40% (w/V) of sucrose acetate isobutyrate.

In an embodiment, the composition may comprise 50-70% (w/V) of the additive selected from chitin, silk fibroin, cellulose, alginate, chitosan, gellan gum, dextrin, collagen, guar gum, carregeenan, heparin, kefiran, or mixtures thereof, preferably 55-65% (w/V) of said additive.

In an embodiment to obtain better results, the sucrose acetate isobutyrate may be dissolved in an ionic liquid, in particular it may be dissolved in an ionic liquid is selected from 1-butyl-3-methylimidazolium chloride, 1-butyl-3-methyl imidazolium acetate, 1-allyl-3-methylimidazolium bromide, 1-ethyl-3-methylimidazolium dimethyl phosphate, 1-carboxymethyl-3-methylimidazolium hydrochloride, 1-ethyl-3-methylimidazolium chloride, 1-ethyl-3-methylimidazolium acetate, or mixtures thereof.

In an embodiment to obtain better results, the sucrose acetate isobutyrate may be dissolved in 1-butyl-3-methylimidazolium chloride [bmim][Cl] and/or 1-butyl-3-methyl imidazolium acetate.

In an embodiment to obtain better results, the additive selected from chitin, silk fibroin, cellulose, alginate, chitosan, gellan gum, dextrin, collagen, guar gum, carregeenan, heparin, kefiran, or mixtures thereof, may be dissolved in an ionic liquid selected from 1-butyl-3-methylimidazolium chloride, 1-butyl-3-methyl imidazolium acetate, 1-allyl-3-methylimidazolium bromide, 1-ethyl-3-methylimidazolium dimethyl phosphate, 1-carboxymethyl-3-methylimidazolium hydrochloride, 1-ethyl-3-methylimidazolium chloride, 1-ethyl-3-methylimidazolium acetate, or mixtures thereof.

In an embodiment and to obtain even better, the additive selected from chitin, silk fibroin, cellulose, alginate, chitosan, gellan gum, dextrin, collagen, guar gum, carregeenan, heparin, kefiran, or mixtures thereof, may be dissolved in an ionic liquid selected from 1-butyl-3-methylimidazolium chloride [bmim][Cl] and/or 1-butyl-3-methyl imidazolium acetate.

In an embodiment, by dissolving the additive and/or the sucrose acetate isobutyrate in an ionic liquid, it is possible to process the additive in such a way that 2D and 3D structures are produced.

In an embodiment and to obtain even better results, it ion according to any one of the previous claims wherein the additive is chitin, silk fibroin, or mixtures thereof.

In an embodiment, the composition of the present subject-matter may also comprise a ceramic additive, in particular wherein the ceramic additive may be selected from hydroxyapatite, bioglass, silicon substituted hydroxyapaptite (HAp), tri-calcium phosphate (TCP), or combinations thereof. The ceramic additive is responsible for bioactivity, biocompatibility, osteoconductivity and/or adequate biodegradability.

In an embodiment, the composition may be the release of the bioactive substance is a sustained release, in particular wherein the sustained release of the bioactive substance is 15 days-6 months, preferably 1-3 months, more preferably 1-2 months.

In an embodiment, the bioactive substance may be selected from a molecule, antibiotic, growth factor, nanoparticles and micro-particles or mixtures thereof. The microparticles are particles between 0.1 and 100 mm in size. The nanoparticles are particles between 1 and 100 nanometers in size.

In an embodiment, the antibiotic may be selected from bacitracin, erythromycin, polymyxin, vancomycin, gentamycin, kanamycin, neomycin, amoxicillin streptomycin, rapamycin, streptomycin, polymyxin, colistin, tyrocidine, gramicidin, cyclosporin, or mixtures thereof.

In an embodiment, the growth factor may be selected from a epidermal growth factor, platelet-derived growth factor, growth hormone releasing factor, platelet derived growth factor, nerve growth factor, or mixtures thereof.

In an embodiment, the nanoparticles may be dendrimers nanoparticles, in particular polyamidoamine (PAMAM).

In an embodiment, the microparticles may be systems of synthetic polymers selected from poly(lactic-co-glycolic acid) (PLGA), poly(lactic acid) (PLA) and/or natural polymers, wherein the natural polymers may be selected from collagen, gelatin, hyaluronic acid, chitosan, trimethyl chitosan, or mixtures thereof.

In an embodiment, the composition now disclosed may be a pharmaceutical composition comprising a pharmaceutically acceptable excipient.

The present disclosure also relates to a composite comprising the composition now disclosed, wherein the composite may be a gel, a membrane or a scaffold.

In an embodiment, the scaffold now disclosed may have a pore size of 0.5-50 µm, preferably 2-20 µm, wherein said pore size was determined by scanning electron microscopy (SEM) or microCT.

This disclosure also relates to a composition or composite for use in medicine.

This disclosure also relates to a composition or composite for use in the treatment or prevention of cartilage disease or defect, skin disease or defect, vascular tissue disease or defect, spinal cord disease or defect, brain diseases or defect or wound healing.

This disclosure also relates to scaffold or membrane comprising the composition or composite of the present disclosure.

The present disclosure also relates to a method of producing a composition or a composite comprising the following steps:
dissolving sucrose acetate isobutyrate in an ionic liquid;
dissolving an additive selected from a polysaccharide, a protein, or mixtures thereof in an ionic liquid;
mixing the dissolved sucrose acetate isobutyrate and the dissolved additive in a solution;
homogenizing the solution;
transferring the solution to a mold;
solidifying;
removing the ionic liquid;
washing of the composition or the composite.

In an embodiment, the method now disclosed may further comprise a step of freeze-drying the composition or composite for obtaining a scaffold, a gel or a membrane.

In an embodiment, the step of mixing may be carried out at 60-120° C., preferably 75-100° C., more preferably at 95° C.

In an embodiment, the step of mixing may be carried out for 5-60 min, preferably 10-30 min, more preferably at 15 min.

In an embodiment, the step of solidifying may be carried out at −80-25° C., preferably −70-4° C., more preferably at −20° C.

In an embodiment, the step of solidifying may be carried out with a solvent is selected from water, isopropanol, ethanol, methanol, tetraglycol (glycofurol), benzyl alcohol, dimethyl sulfoxide, ethyl lactate, ethyl acetate, triacetin, N-methylpyrrolidone, propylene carbonate, glycerol formal, isopropylideneglycerol, or mixtures thereof.

In an embodiment, the solvent may be water or water:isopropanol (1:1).

In an embodiment, the ionic liquid may be independently selected from 1-butyl-3-methylimidazolium chloride, 1-butyl-3-methyl imidazolium acetate, 1-allyl-3-methylimidazolium bromide, 1-ethyl-3-methylimidazolium dimethyl phosphate, 1-carboxymethyl-3-methylimidazolium hydrochloride, 1-ethyl-3-methylimidazolium chloride, 1-ethyl-3-methylimidazolium acetate, or mixtures thereof.

BRIEF DESCRIPTION OF THE DRAWINGS

The following figures provide preferred embodiments for illustrating the description and should not be seen as limiting the scope of invention.

FIGS. 6A-6B.

FIGS. 9A-9C. SAIB scaffolds cytotoxicity.

TABLE 1

Adhesivity values obtained for Chitin and SAIB/Chitin gels (in water, solvent

| SAMPLE | ADHESIVITY (N · s) |
|---|---|
| SAIB/CHITIN A | 0.135 ± 0.003 |
| CHITIN A | 0.035 ± 0.002 |

TABLE 2

Morphological features of the chitin and chitin/SAIB-based scaffolds from microCT essays.

| SAMPLE | POROSITY (%) | INTER-CONNECTIVITY (%) | MEAN WALL THICKNESS (µM) | MEAN PORE SIZE (µM) |
|---|---|---|---|---|
| CHITIN A | 88.58 | 98.52 | 20.52 | 101.4 |
| CHITIN B | 81.74 | 95.61 | 23.96 | 77.59 |
| CHITIN/SAIB A | 46.57 | 14.53 | 56.34 | 57.80 |
| CHITIN/SAIB B | 57.43 | 54.40 | 50.06 | 60.21 |

DETAILED DESCRIPTION

The present disclosure relates to a composition for the release of the bioactive substance comprising: sucrose acetate isobutyrate dissolved in an ionic liquid and an additive selected from the list consisting of: chitin, silk fibroin, cellulose, alginate, chitosan, gellan gum, dextrin, collagen, guar gum, carregeenan, heparin, kefiran, or mixtures thereof. By taking advantage of the properties of an ionic liquid (IL), in particular 1-butyl-imidazolium acetate (BMIMAc), it was possible to achieve a good dissolution of SAIB, which combined with chitin and/or silk, natural polymers, allows the development of the structures with different shape and sizes.

In an embodiment, the materials used were the following: chitin from crab shells (practical grade; Sigma Aldrich) with a degree of N-acetylation of 57.9%, determined by elemental analysis, were ground through a Wiley Mill (model 4, Thomas) and stored in plastic bottles. Ground chitin (106 m) was used throughout the experiments to obtain reproducible results. SAIB and the ionic liquid (IL), 1-Butyl-3-methyl-imidazolium chloride [bmim][Cl] and 1-butyl-3-methyl imidazolium acetate [bmim][Ac], used without further purification, were obtained from Sigma Aldrich. Silk fibroin from cocoons of B. mori was kindly supplied by the APPACDM (Castelo Branco, Portugal) Genipin was purchased from Wako Chemicals. All other chemicals were reagent grade and were used as received.

In an embodiment, the preparation of the SAIB/chitin based structures was carried out as follows: SAIB (0.4 g·mL$^{-1}$) and chitin (0.01 g·mL$^{-1}$) were dissolved individually in [bmim][Ac], at 75° C. and 95° C., respectively, and then homogenized in the ratio 50/50 by adding the SAIB/IL solution to the chitin/IL solution. After homogenization (about 15 min), the solution was transferred to silicone molds (d=8 mm, h=2 mm), followed by gelation of the systems through their immersion in water (solvent A) or water:isopropanol (1:1, solvent B) to obtain the chitin/SAIB gels. Moreover, membranes were also produced using bigger molds (d=3 cm). The [bmim][Ac] removal procedure was first carried out by immersing the materials in the solvents A and B for 48 hours followed by Soxhlet extraction with the same solvents. In the optimization stage, the Soxlet was replaced by a coarser but equally effective procedure. After 48 h in the molds, and immersed in the solvents, the structures were placed in caped flasks at 150 rpm with daily solvent change (5 days). During this washing step, aliquots were collected to measure the conductivity and thus follow the removal of the ionic liquids throughout time. This method is schematically represented on FIG. 1.

A similar procedure was used and optimized to prepare SAIB/Silk fibroin (SAIB/SF) structures. Briefly, SAIB (0.4 g·mL$^{-1}$) and SF (0.1 g·mL$^{-1}$) were dissolved individually in [bmim][Ac], at 75° C. and 60° C., respectively, and then homogenized in the ratios 1:1, 1:2 and 2:1 SAIB:SF by adding the SAIB/IL solution to the SF/IL solution. After homogenization (about 15 min), the solution was transferred to silicone molds (d=8 mm, h=2 mm), followed by gelation of the systems at −20° C. for 2 hours. Further, the systems [bmim][Ac] removal procedure and beta sheet formation were carried out by immersing the systems in water/isopropanol 1:1 (solvent B), water/methanol 1:4 and water.

Moreover, taking advantage of the acquired knowledge on the developed SAIB/chitin structures and also of the genipin properties, genipin crosslinked SAIB/chitin membranes were also produced. The developed and optimized procedure started by using SAIB (0.4 g·mL$^{-1}$) and chitin (0.1 g·mL$^{-1}$) dissolved individually in [bmim][Ac], at 75° C. and 95° C., respectively, and then homogenized in the ratio 50/50 by adding the SAIB/IL solution to the chitin/IL solution. After homogenization (about 15 min), the solution was transferred to small petri dishes, followed by gelation of the systems at −20 C during 2 hours. To create crosslinked SAIB/chitin membranes, the systems were immersed in genipin solutions (10 mM, 20 mM), prepared using ethanol/water, for 24 hours at room temperature (RT) and 4° C. After that, the materials were immersed in water (solvent A) or water:isopropanol (1:1, solvent B) to obtain the crosslinked chitin/SAIB gels. During IL removal, aliquots were collected to measure the conductivity and thus follow the removal of the ionic liquids throughout time. In an embodiment, to obtain SAIB/Chitin and SAIB/SF based scaffolds, SAIB/Chitin and SAIB/SF gels were freeze-dried.

In an embodiment, to obtain porous SAIB/Chitin based membranes the crosslinked chitin/SAIB gels were freeze-dried.

In an embodiment, the physicochemical characterization of the SAIB/Chitin, SAIB/SF and porous SAIB/Chitin membranescaffolds was carried out.

In an embodiment, the conductivities of the collected aliquots, of the washing solvents throughout time, were measured using a conductivimeter (INOLAB, Multi-level 3) with a Sonda WTW TetraCon 325.

In an embodiment, Fourier transform infrared spectroscopy (FTIR) was carried out. The specimens to be analyzed were powdered and mixed with potassium bromide, milled and molded into a transparent pellet using a press (Pike, USA). Transmission spectra were acquired on an IR Prestige-21 spectrometer (Shimadzu, Japan), using 32 scans, a resolution of 4 cm$^{-1}$ and a wavenumber ranging between 4000 cm$^{-1}$ and 500 cm$^{-1}$.

In an embodiment, X-ray diffraction (XRD) patterns were determined. The qualitative analyses of crystalline phases presented on the hydrogels were assessed by XRD using a conventional Bragg-Brentano diffractometer (Bruker D8 Advance DaVinci, Germany) equipped with CuKα radiation, produced at 40 kV and 40 mA. Data sets were collected in the 2Θ range of 5-60° with a step size of 0.02° and is for each step.

In an embodiment, scanning electron microscopy (SEM) was carried out. The freeze-dried samples were attached to aluminum stubs using a carbon tape and coated with platinum in a sputter coater (Model EM ACE600, Leica, Germany). The morphology images were obtained on a SEM (JSM-6010LV, JEOL, Japan), featuring integrated energy dispersive spectroscopy (EDS) (INCAx-Act, PentaFET Precision, Oxford Instruments).

In an embodiment, the microstructure of the prepared SAIB/chitin-based scaffolds was evaluated using a high-resolution X-ray microtomography system Skyscan 1072 scanner (Skyscan, Kontich, Belgium). Samples were scanned using a pixel size of 8.79 mm x/y/z and an X-ray source fixed at 40 keV of energy and 248 mA of current. After the acquisition, reconstructed grey-scale images were converted into binary images by using a dynamic threshold of 40-255. Then, the binary images were used for morphometric analysis (CT Analyzer v1.12.0.0, SkyScan, Kontich, Belgium) by quantification of porosity, mean pore size, mean wall thickness and interconnectivity. In an embodiment, swelling tests were made. The dry samples weight was measured ($W_D$) and, after immerse in PBS and remove the excess of water (by softly tapping the surface with filter paper), the samples wet weight ($W_S$) was measured. The samples were rehydrated until equilibrium. The degree of swelling was determined by calculating $(W_S-W_D)/W_D$. Each experiment time point was repeated 3 times.

In an embodiment, pull away experiments were performed using a Kinexus pro+ rheometer (Malvern Instruments, UK), using the acquisition software rSpace. The measuring system used in these experiments was equipped with stainless steel (316 grade) plate-plate system. These experiments involved loading a sample and then pulling away the upper plate at a defined gap speed ($1 \text{ mm} \cdot \text{s}^{-1}$), with a contact time of 2 s and a contact force of 1 N. The resultant normal force was then recorded as function of gap and was used to determine the adhesion properties (area under the force-gap curve).

In an embodiment, cell growth was assessed using the CellTiter 96® AQueous One Solution Cell Proliferation Assay (MTS, Promega, USA). At each time point, 24 hours, 48 hours and 72 hours cells were incubated with 20% V/V of MTS in culture medium without phenol red (Sigma Aldrich, USA) for 3 hours at 37° C. The supernatant was then transferred to a new 96-well plate and absorbance measurements were carried out using a microplate reader (Biotek Synergy HT) at 490 nm.

In an embodiment, cell damage was studied through F-actin staining. For that, cells were washed with phosphate buffer saline (PBS, Sigma Aldrich, USA), fixed with 10% Neutral Buffered Formalin (ThermoFisher Scientific, USA) for 15 minutes and permeabilized for 5 minutes with 0.1% V/V Triton X-100 (Sigma Aldrich, USA) in PBS. Afterwards, samples were incubated for 30 minutes in 1% (w/V) of BSA (Sigma Aldrich, USA) in PBS to block unspecific binding. F-actin filaments were stained with Phalloidin-Tetramethylrhodamine B isothiocyanate (1:40, Sigma Aldrich, USA) and nuclei were counterstained with 1:5000 of the stock of 4,6-Diamidino-2-phenyindole, dilactate solution (DAPI, 1 mg/mL, Biotium, USA). Samples were analysed under a fluorescence inverted microscope (Zeiss Axio observer).

In an embodiment, cytotoxicity screening of the SAIB/Chitin based scaffolds were performed. Human adipose derived stem cells (hASCs) were obtained from human adipose tissue after liposuction procedure, which was performed at Hospital da Prelada (Porto, Portugal), after patient's informed consent and under a collaboration protocol approved by the ethical committees of both institutions. In order to isolate the hASCs, the adipose tissue was submitted to the action of 0.05% collagenase type II (Sigma Aldrich, USA), under agitation for 1 hour at 37° C. Then, it was filtered with a strainer and centrifuged at 800 G for 10 minutes. After discard the supernatant, pellets were re-suspended in PBS and centrifuged at 350 G for 5 min. Finally, the cell pellet was re-suspended in Minimum Essential Media α (α-MEM, Gibco, UK), supplemented with 10% fetal bovine serum (FBS, Invitrogen, USA), and 1% antibiotic/antimycotic (Invitrogen, USA). Cultures were maintained at 37° C. under a humidified atmosphere of 5% V/V $CO_2$ in air. hASCs were selected by plastic adherence and passage at 80% confluence. In the different studies hASCs in passage 4 were used.

In an embodiment, the evaluation of cytotoxicity of SAIB/Chitin based scaffolds was performed as described in the ISO 10993-12, using hASCs. First, hASCs were seeded in each well of a 96-well plate at a density of 3000 cells per $cm^2$. After 24 hours of culturing, the SAIB/Chitin based scaffolds produced using solvent A and solvent B (SAIB/Chitin A and SAIB/Chitin B, respectively) were added to the top of cells. As control, Chitin scaffolds produced using solvent A and B were tested (Chitin A and Chitin B, respectively). Additionally, a negative control (Ctrl-) was prepared composed of hASCs without addition of scaffolds and a positive control (Ctrl+) composed of Triton X-100 at a concentration of 1% in culture medium. Cultures were maintained at 37° C. under a humidified atmosphere of 5% V/V $CO_2$ in air. Finally, at 24, 48 and 72 hours of culture, cell growth and cell damage were analysed as described previously.

In an embodiment, cell morphology: whole-mounted samples were evaluated. At different time points scaffolds were recovered and F-actin was stained to evaluate cell morphology. For that, samples were washed with PBS, fixed with 10% Neutral Buffered Formalin for 15 minutes and permeabilized for 5 minutes with 0.1% V/V Triton X-100 in PBS. F-actin filaments were stained with Phalloidin-Tetramethylrhodamine B isothiocyanate (1:80) and nuclei were counterstained with DAPI (1:5000). Controls analyzed under a fluorescence inverted microscope (Zeiss Axio observer) and samples were analyzed using confocal microscopy (Leica TCS SP8).

In an embodiment, statistical analyses was performed using GraphPad Prism 6.0 software. The non-parametric Mann-Whitney test was used to compare two groups, whereas comparison between more than two groups was performed using the Kruskal-Wallis test followed by Dunn's comparison test. Additionally, a two-way ANOVA followed by Tukey's multiple comparisons test was used every time that studies involved two independent variables. The critical level of statistical significance chosen was $p<0.05$. Data of 3 experiments are presented as mean±SEM. In an embodiment, the physicochemical characterization of scaffolds and membranes produced and herein disclosed was carried out as follow.

Figure 2:
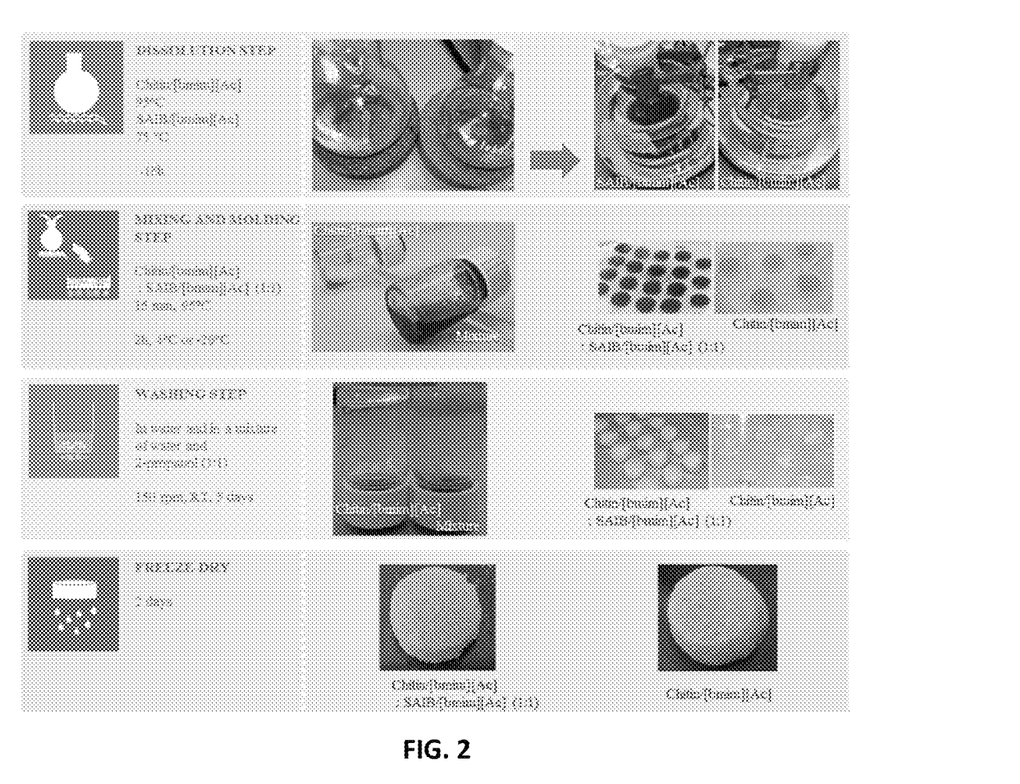
FIG. 2. Schematic representation of the production steps, together with some example images.

In an embodiment, the SAIB/Chitin based scaffolds were produced as herein described and schematically shown on FIG. 2. The preliminary experiments showed that SAIB not only is able to dissolve in [bmim][Ac] but also to blend with other compounds dissolved in IL, in particular chitin/IL or silk fibroin/IL.

In an embodiment, it was also observed that SAIB does not dissolve in [bmim][Cl] neither is able to form gels alone in [bmim][Ac]. Concerning the used solvents A (water) and B (water:isopropanol 1:1), those were chosen, after testing ethanol, methanol and others, concerning what was visible to the naked eye (e.g. do not dissolve the gel, able to clean the ionic liquid, . . . ). Therefore, the subsequent experiments were performed by mixing SAIB/IL in Chitin/IL (95° C., 15 min), after the dissolution step where SAIB and Chitin were separately dissolved in the IL (18 hours approximately). It was noticed that, mixing SAIB/IL in Chitin/IL and mixing Chitin/IL in SAIB/IL was slightly different, apparently having the first a better mechanical behavior in the end of the process. Temperatures for the first 2 hours of molding were also tested, room temperature and 4° C. showed weaker gels that disintegrate during the washing step (FIG. 2) while at −20° C. the gels showed a better behavior maintaining the shape unbroken.

Figure 3A:
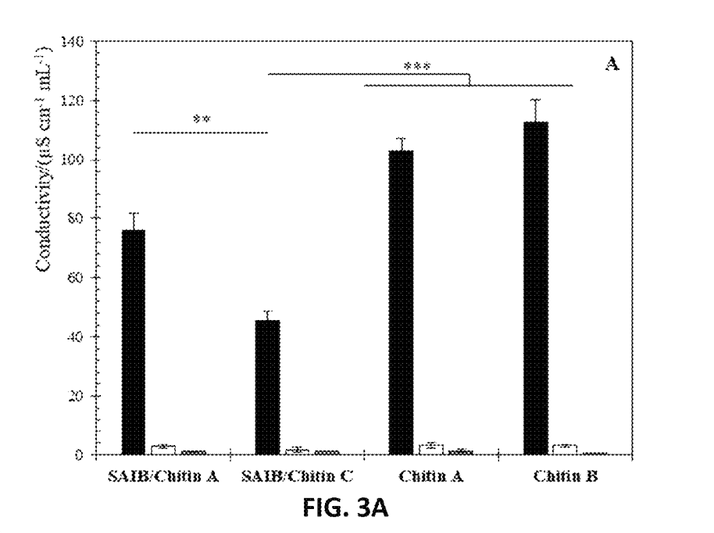
FIGS. 3A-3B. Conductivity measurements on aliquots of the washing step solvents, obtained after immersion of the structures with 150 rpm of agitation, on the first day (black bars), second day (white bars) and $5^{th}$ day (gray bars), wherein for FIG. 3A, SAIB/Chitin A stands for SAIB processed with [bmim][Ac] and mixed with Chitin processed with [bmim][Ac] in water (solvent A), SAIB/Chitin B stands for SAIB processed with [bmim][Ac] and mixed with Chitin processed with [bmim][Ac] in water:isopropanol (1:1) (solvent B), Chitin A stands for chitin processed with [bmim][Ac] in water (solvent A); Chitin B stands for chitin processed with [bmim][Ac] in water:isopropanol (1:1) (solvent B). In the same way, for FIG. 3B, SF B and C stands for silk fibroin (SF) scaffolds processed with solvent B (isopropanol:water 1:1) and C (methanol:water 1:1) and SAIB:SF 1:1, SAIB:SF 1:2 and SAIB:SF 2:1 the different proportions of SAIB to SF, in the same solvents B and C. Data represent the mean±standard deviation (significant differences $p<0.05$, two-way ANOVA).

In an embodiment, in the washing step, using the Soxhlet installation and procedure (1 L solvent per day), the gels were cleaned within 3 days, while when just placed in 50 mL-flasks (50 mL solvent), it takes 8 days. Though, in 100 mL-flasks with agitation (150 rpm) the samples were clean of ionic liquid within 5 days, which make a good compromise between time and efficiency, especially in the optimization stage, since it is conceivable to clean several lots of samples (with 5 mL of solvent per gel) at once, using 100 mL per day (FIG. 3A).

Figure 3B:
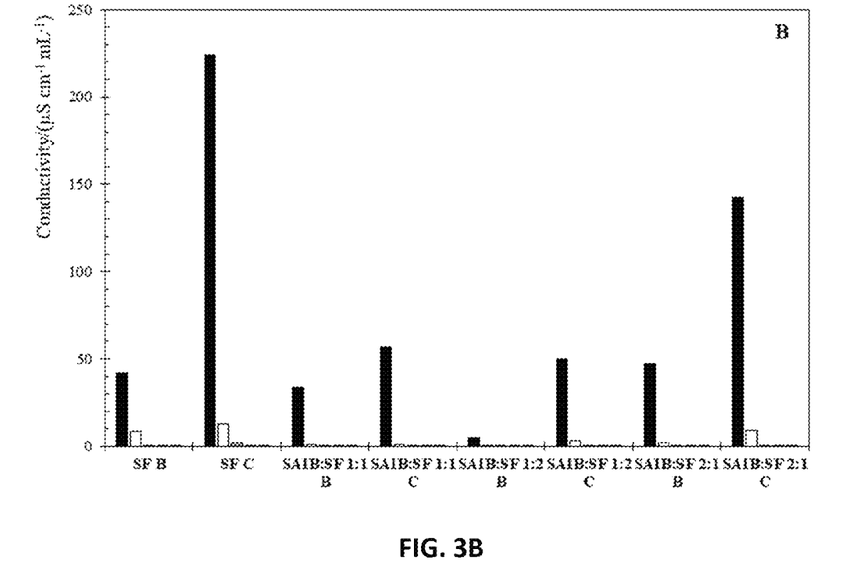

In an embodiment, the SAIB/SF gels were produced and washed following the same previous procedure (FIG. 2) and the conductivity measurements were also performed (FIG. 3B), where the solvent B is a mixture of water:isopropanol (1:1) and C is a mixture of water:methanol (1:1) are the used washing solvents.

Figure 4:
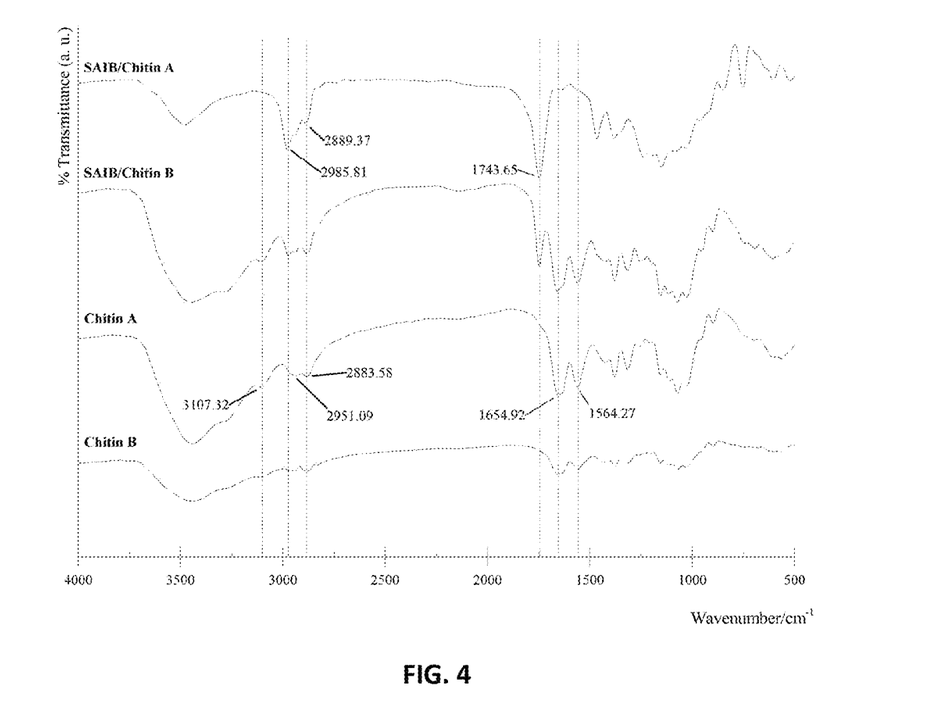
FIG. 4. FTIR spectra of SAIB/Chitin and Chitin samples processed with [bmim][Ac] in water (A), and in water:isopropanol (1:1) (B).

From FIG. 4, it is possible to observe the FTIR spectra of SAIB/Chitin mixture and Chitin samples, processed with [bmim][Ac] in water (A) and in water:isopropanol (1:1)(B).

In an embodiment, the FTIR spectra of [bmim][Ac] and the native chitin used in this disclosure was already reported. Comparing those, with the ones obtained for the produced scaffolds it is possible to observe that the absorption bands characteristic for [bmim][Ac] (~1400 $cm^{-1}$, 1180 $cm^{-1}$ and 1020 $cm^{-1}$) are not present on the studied samples, appointing to a good removal of the ionic liquid. Concerning the native chitin spectra, it is possible to observe the most characteristic bands and easier to detect on the amide region (specifically, at ~1655 $cm^{-1}$ and 1564 $cm^{-1}$). These peaks, together with one more vanished at around 1628 $cm^{-1}$, are assigned to the stretching of the C=O groups bonded to N—H groups of the adjacent chain, the stretching of the C=O groups diverged by forming an additional hydrogen bond to the primary OH groups of the same chain, and NH deformations, respectively [4]. Concerning the pure SAIB spectra, a strong IR absorption denotes a relevant peak for SAIB identification, at 1744 $cm^{-1}$. The carbonyl (C=O) absorption between 1690-1760 $cm^{-1}$ indicates either an aldehyde, ketone, carboxylic acid, ester, amide, anhydride or acyl halide. Concerning the SAIB structure, this strong band is relative to its ester carbonyl stretching absorption.

In an embodiment, comparing the scaffolds analyzed, Chitin/IL scaffolds prepared in (A) water or in (B) the mixture of water and isopropanol (1:1) (Chitin A and Chitin B, FIG. 4) are very similar. Though, the blends of SAIB/IL and Chitin/IL in both solvents are quite different regarding the chitin presence. In fact, in water seams that the SAIB bands are more intense, while in the mixture water:isopropanol the presence of chitin is more remarked. That could be explained by the SAIB good solubility in organic solvents. Thus, besides SAIB/Chitin A and SAIB/Chitin B being prepared with the same proportions of SAIB/IL and Chitin/IL, some of the SAIB in the solvent B was lost, while in the solvent A it remained and more intense peaks are perceived.

Figure 5:
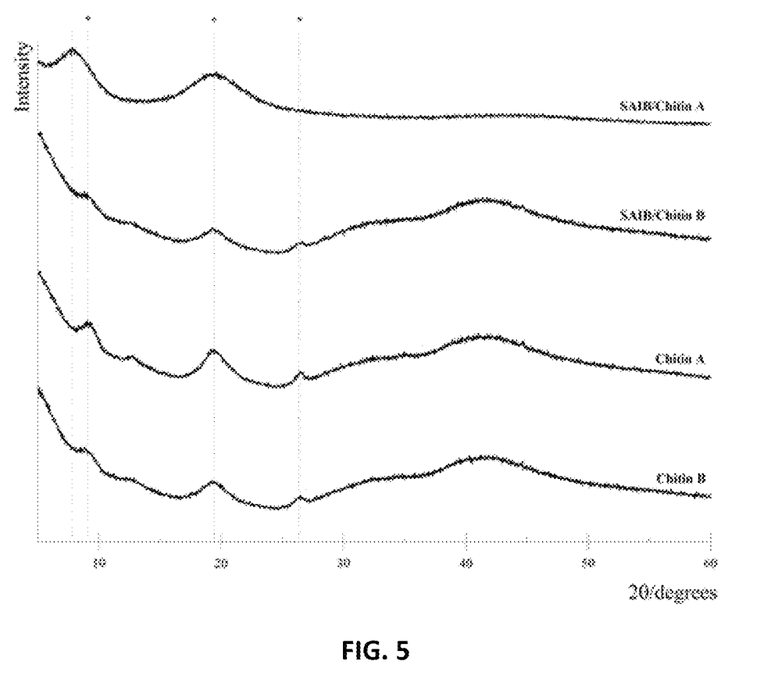
FIG. 5. XRD patterns of SAIB/Chitin and Chitin samples processed with BMIMAc, in water (A) and in water:isopropanol (1:1)(B).

In an embodiment, the XRD patterns of the scaffolds are depicted in FIG. 5.

In an embodiment, FIG. 5, it can be observed the main characteristic peaks of the chitin crystalline phase [5] at 2θ=9.1°, 19.3° and 26.4°, associated to (020), (110) and (013) crystallographic planes, respectively. The peaks at 9.1° and 19.3° can be specifically endorsed to glucosamine sequences and N-acetyl-D-glucosamine monomers of chitin [4]. It can also be observed that the presence of SAIB in the scaffolds can affect the crystallinity. This effect is particularly observed in SAIB/Chitin A scaffold, where no SAIB has been lost to the solvent and therefore SAIB is more concentrated. This is in accordance with the literature, where SAIB is known as a monocrystalline ester, being thus anticipated a reduction on the crystallinity of the mixture.

Figure 6A:
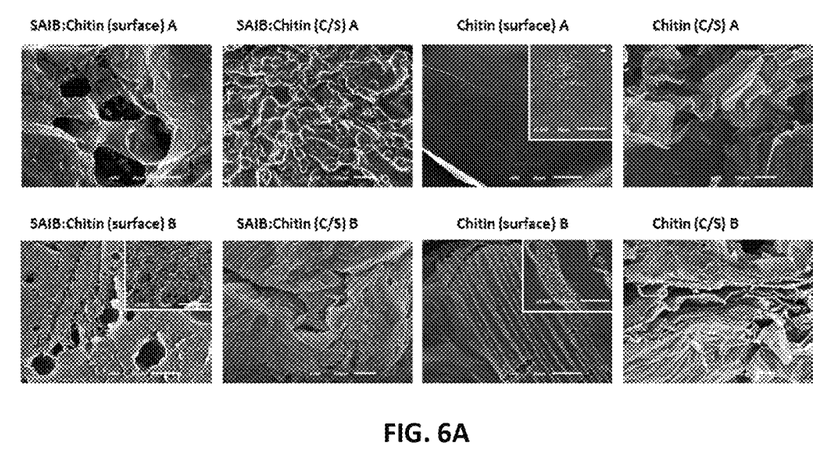
FIG. 6A: SEM images of surface and cross-section (C/S) of the scaffolds:SAIB:Chitin and Chitin samples processed with BMIMAc, in water (A) and in water:isopropanol (B).
Figure 6B:
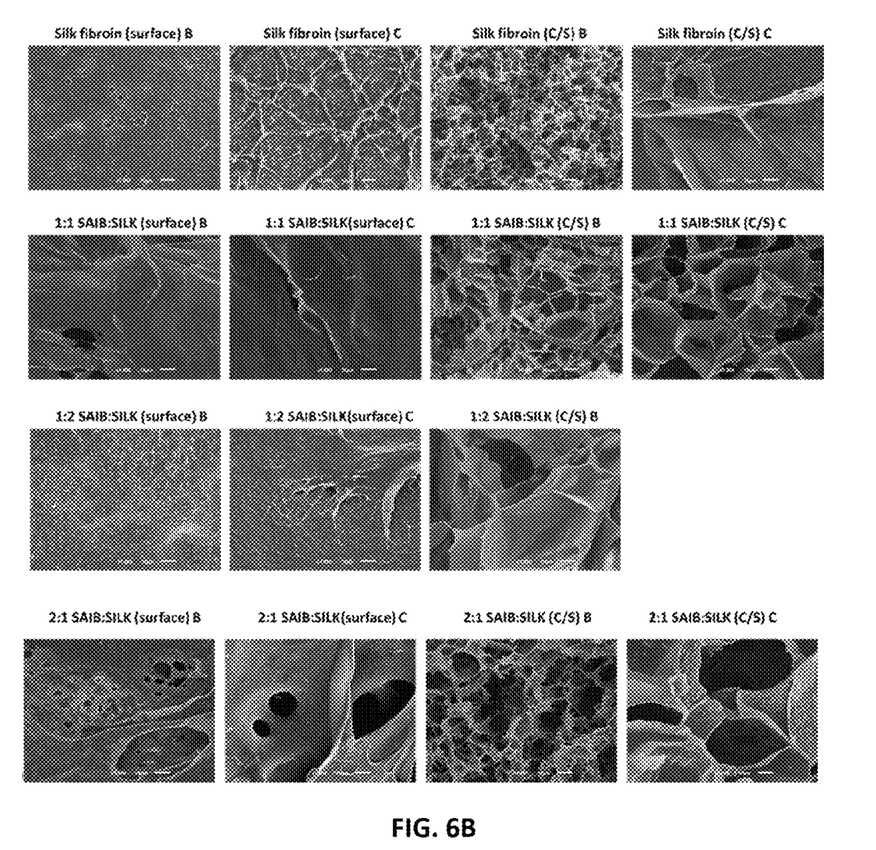
FIG. 6B: SEM images of surface and cross section (C/S) of the scaffolds with different proportions of SAIL:Silk fibroin (1:1, 1:2 and 2:1) processed with BMIMAc, in water:isopropanol (B) and water:methanol (C).

In an embodiment, the morphology of the scaffolds (mixtures of chitin/IL or SF/IL and SAIB/IL and just chitin/IL), in solvents A, B and C (SAIB/chitin A, SAIB/chitin B, Chitin A and Chitin B or even SAIB/SF B and SAIB/SF C), was observed by SEM, for the surface (S) and also for the cross-sections (C/S) (FIGS. 6A and 6B).

In an embodiment, the obtained micrographs (FIGS. 6A-6B) suggest that the scaffolds with SAIB (A and B, FIG. 6A) are denser than the ones without it. Nonetheless, the sample SAIB/chitin B (B1 and B2, FIG. 6A), possibly due to the already referred slight loss of SAIB to the isopropanol, has some opening cracks as well as some fibrous regions (B1 ×2000, FIGS. 6A-6B). Moreover, the cross-section of the sample B1 shows a morphology that resembles the typical morphology of aerogels. The observed pore size of the samples also revealed the effect of both compounds. In fact, when SAIB is present bigger pore sizes are observed 80±26/54±19 μm (length/width) for SAIB/Chitin A, 36±23/28±20 μm but also another group of sizes 1.6±1.1/1.2±0.8 μm (length/width) for SAIB/Chitin B. Nevertheless, for chitin in water (Chitin A) the bigger pores were observed 203±135/102±89 μm (length/width), mainly due to the solvent used, water. When the solvent is the mixture water:isopropanol (1:1) smaller pores are obtained for chitin (Chitin B), as well as a better distribution, 0.55±0.29/0.40±0.23 μm (length/width).

In an embodiment, both silk and SAIB/SF based scaffolds were successfully produced using the methodology applied to SAIB/chitin based materials. However, the solvents used in the gelation and IL removal were changed to promote the beta sheet formation into the materials. The SEM images of the cross sections of the scaffolds (FIG. 6B) indicated that both silk and SAIB/SF have an open structure. Differences in the morphology of the scaffolds were observed probably due to the partial dissolution of the SAIB during the processing.

Figure 7A:
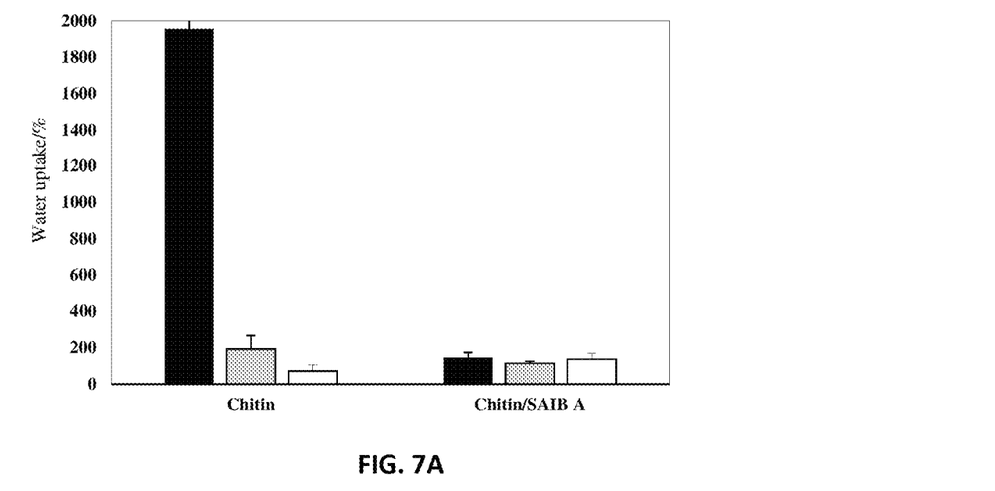
FIGS. 7A-7B. Swelling behavior of the SAIB/chitin (FIG. 7A) and SAIB/SF (FIG. 7B) scaffolds. Data represent the mean±standard deviation (*** denotes the statistical significant differences $p<0.003$, two-way ANOVA).
Figure 7B:
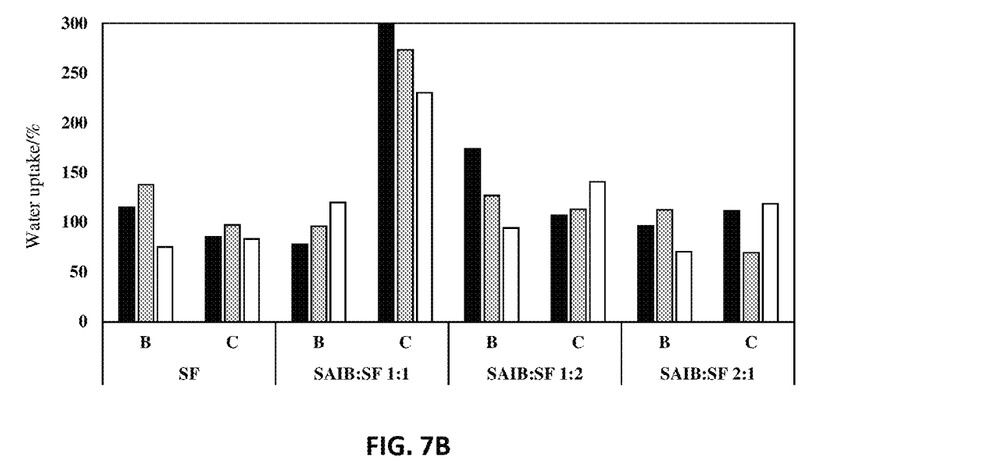
Figure 8A:
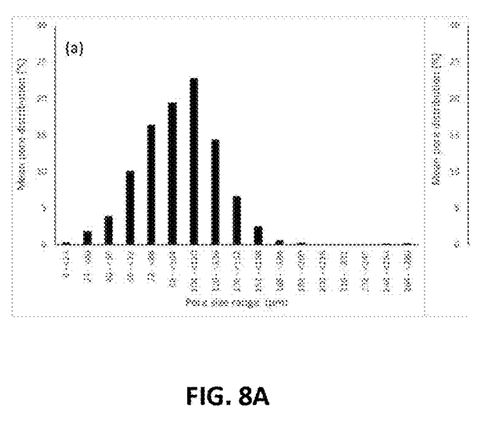
FIGS. 8A-8D. Pore size distribution of chitin scaffolds and SAIB/Chitin based scaffolds: chitin A (FIG. 8A), chitin B (FIG. 8B), SAIB/chitin-A (FIG. 8C) and SAIB/chitin B (FIG. 8D). Data obtained from the micro-CT analysis.
Figure 8B:
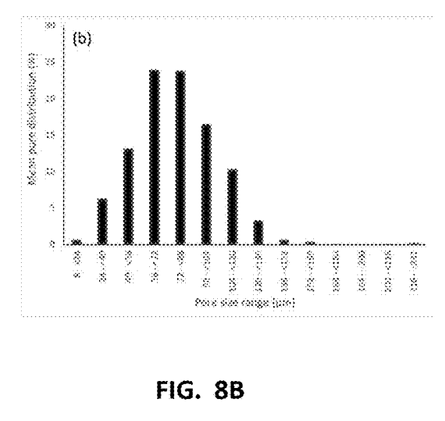
Figure 8C:
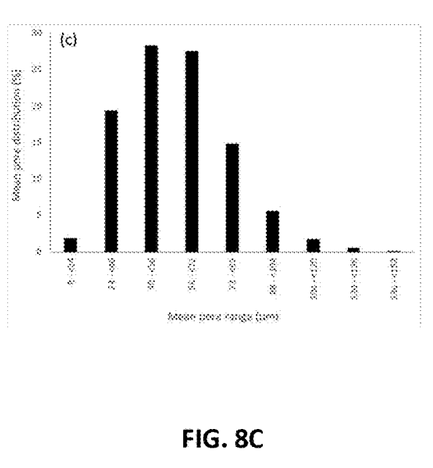
Figure 8D:
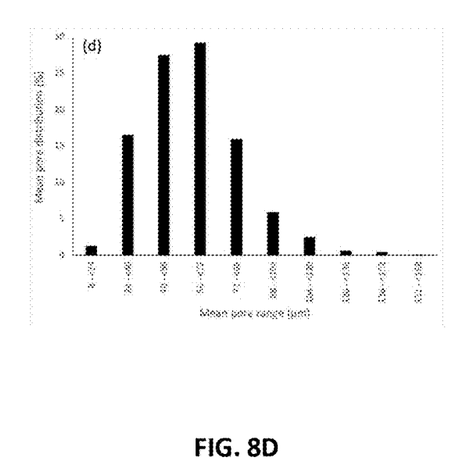

In an embodiment, the swelling procedure for SAIB/chitin and SAIB/SF scaffolds was also performed at the timepoints of 15 min, 7 h and 24 h. FIGS. 7A and 7B shows the swelling ratio obtained for each sample. In an embodiment, the swelling studies on the scaffolds produced were performed, in PBS, to understand the water uptake ability. It is possible to observe a significant difference between the SAIB/Chitin and the Chitin. It is possible to observe that the presence of SAIB prevented the entrance of water on the structure (FIG. 7A).

In an embodiment, the water uptake of the SAIB/SF scaffolds (FIG. 7B) showed different swelling degree. In fact, these results could be related to 3-sheet crystalline content within the matrices, which may have a significant role in their stability when incubated in PBS. Once again, the SAIB presence showed to prevent the entrance of water resulting in the stabilization of the water uptake throughout time.

In an embodiment, pull away tests to Chitin and SAIB/Chitin gels (in water, solvent A) allowed us to state that the presence of SAIB contributes to an increase of adhesivity (4 times), Table 1. This feature could be useful to help bacterial cells for adhesion to biological surfaces and biofilm formation. The advances in biofilm formation knowledge, coupled with emerging engineered biomaterials, provide many potential platforms and strategies to prevent or significantly reduce biofilm infections.

In an embodiment, micro-CT analysis was used to obtain quantitative information of the 3D architecture of the chitin and chitin/SAIB based scaffolds (Table x2). Table 2 demonstrates that chitin scaffolds presented both high porosity and interconnectivity. Moreover, the values of porosity and interconnectivity of SAIB/chitin-based scaffolds were lower than chitin scaffolds. The differences on morphological features of SAIB/chitin-based scaffolds can be associated to partial dissolution of SAIB during their processing. The micro-CT morphometric analysis revealed a widespread pore size as shown in FIGS. 8A-8D. Overall, the morphological features of the developed scaffolds may help homogeneous cell distribution and transfer of nutrients effectively, as well as to facilitate cell growth within the 3D porous structures.

Figure 9A:
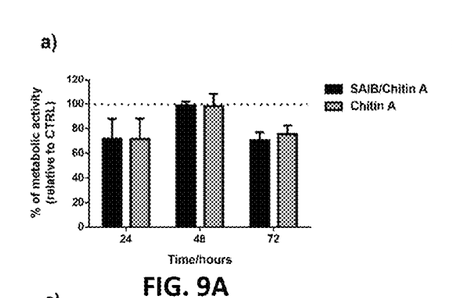
FIG. 9A: Cells' growth of hASCs cultured during 72 hours directly with SAIB/Chitin A and Chitin A scaffolds. Results are present as percentage in relation to CTRL. Data is presented as mean±SEM.
Figure 9B:
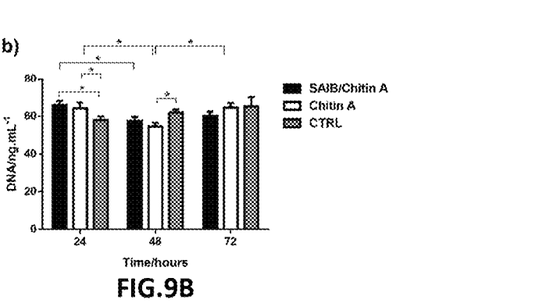
FIG. 9B: Quantification of hASCs' proliferation upon culture directly with SAIB/Chitin A and Chitin A scaffolds along 72 h of culture. Data is presented as mean±SEM. * denotes statistically significant differences ($p<0.05$).
Figure 9C:
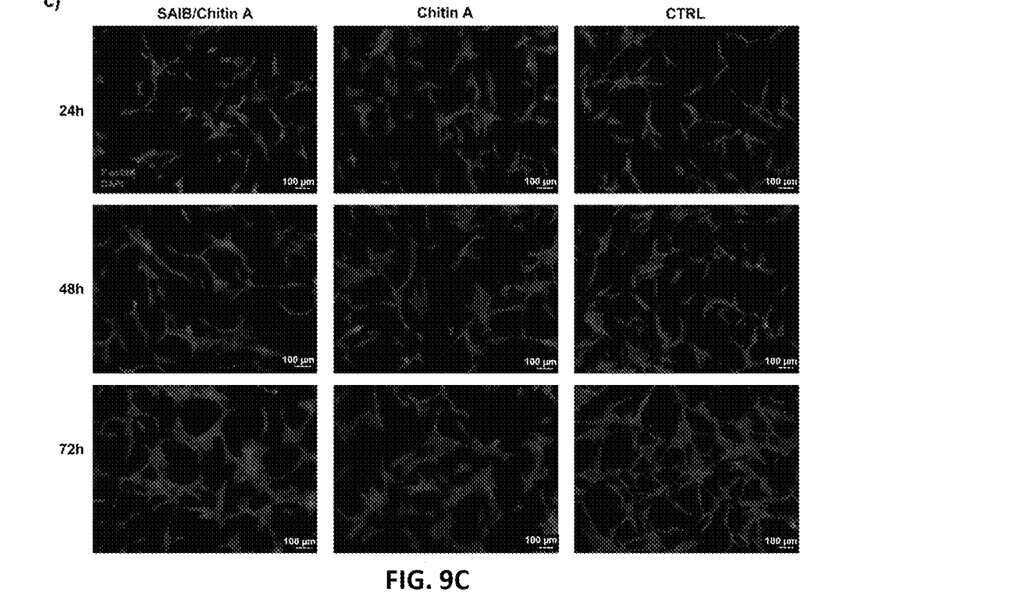
FIG. 9C: Cells' damage assessed by F-actin staining (cytoskeleton, red) and counterstained with DAPI staining (nuclei, blue), during 72 hours of culturing (scale bar: 100 m).

In an embodiment, to assess cytotoxicity of SAIB scaffolds by direct contact, hASCs were used to provide a more physiologically relevant environment. In FIGS. 9A-9C, it is depicted cell growth evaluated by metabolic activity determination using MTS assay, cell proliferation assessed by dsDNA quantification, and cell damage observed by F-actin staining, along the time of culture. In relation to cells growth (FIG. 9A), no statistical differences were observed along the time of culture between SAIB/Chitin A and Chitin A. But it was noticeable that cells' metabolic activity was lower after 24 h of culture when comparing with CTRL, reaching values similar after 48 h, but decreasing again to initial values after 72 h. In other hand, considering dsDNA quantification (FIG. 9B), it was observed an opposite trend. In fact, it is evident that cells' proliferation rates were higher after 24 h in contact with SAIB/Chitin A and Chitin A comparing with CTRL, but they decreased after 48 h. After 72 h of culture cells' proliferation increased and were similar to all conditions. These observations indicated that during 48 h cells were adapting to the scaffolds, which make them more metabolic active and less proliferative. Nevertheless, after 72 h of culture, cells were completely adapted, as demonstrated by the decrease on their metabolic activity and increase on proliferative rates. Additionally, F-actin staining (FIG. 9C) showed that the culturing of cells directly with each scaffold did not promote any visible cell damage, corroborating previous observations. Worth mentioning, as Ctrl+ was equal to zero it was withdrawn from the results to simplify its analysis, only CTRL was kept.

Figure 10:
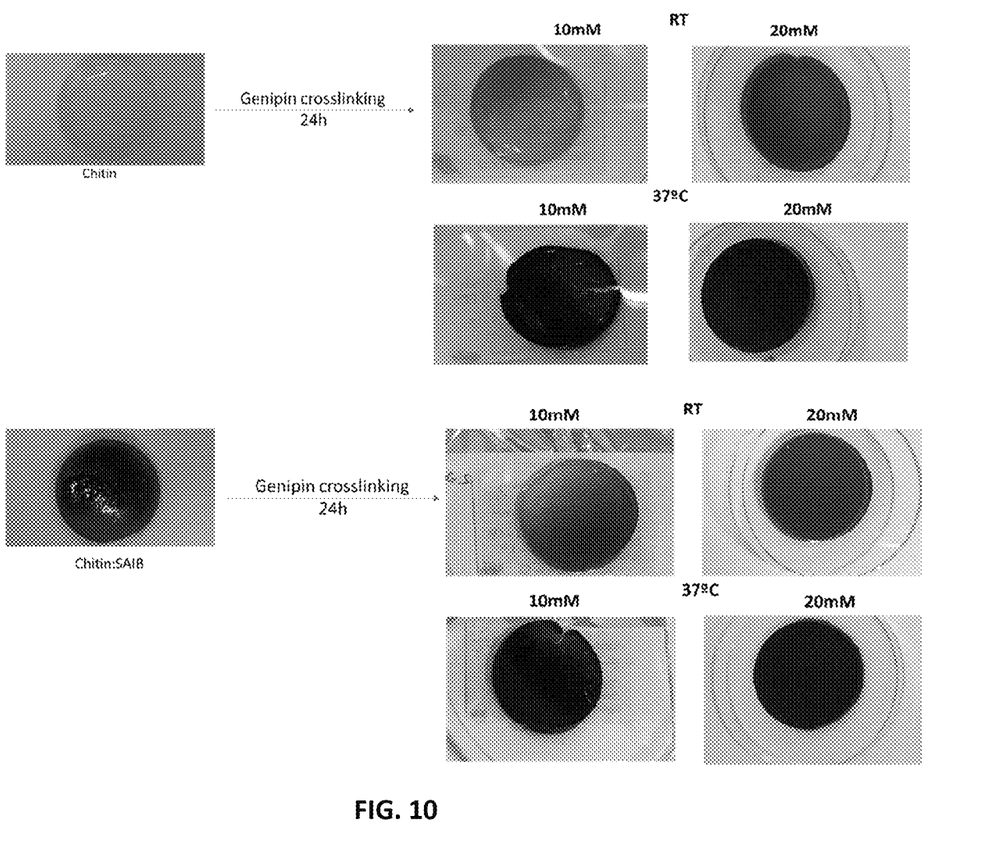
FIG. 10. Chitin and SAIB/chitin based membranes photos, before and after genipin crosslinking.

In an embodiment, chemical crosslinking on SAIB/chitin membranes was investigated as an approach to increase the stability of the blends which will imply in an improvement of their physical properties. Genipin, a natural crosslinker, was chosen to perform the crosslinking reactions on SAIB/chitin membranes. Genipin can react with amino, carboxyl and hydroxyl groups. In our work, we hypothesize that genipin will react with amino groups present into chitin. Both genipin crosslinked chitin and SAIB/chitin-based membranes were successfully prepared as shown in FIG. 10. The results showed that crosslinked membranes presented colour changes during the reaction, namely from slight yellowish color (chitin membrane) and brown colour (SAIB/chitin) to green, then to dark green.

Figure 11:
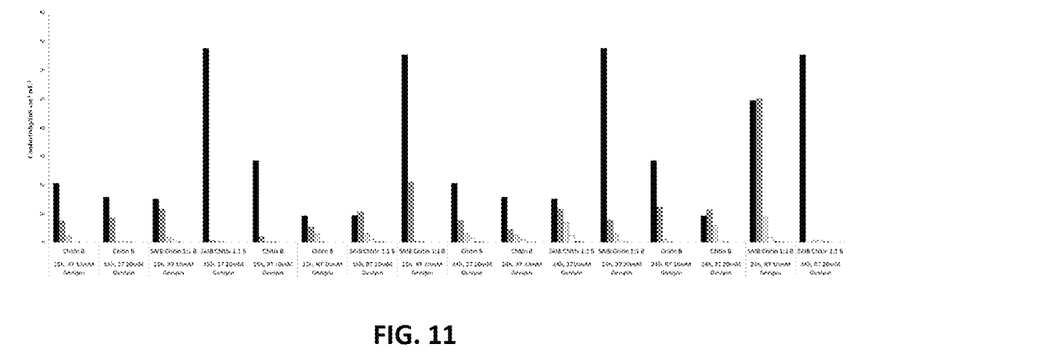
FIG. 11. Conductivity measurements measured during IL removal, on the first day (black bars), second day (gray bars) and $5^{th}$ day (white bars).

In an embodiment, the membranes were almost clean after 3 days (FIG. 11), and a complete removal was achieved after 6 days. Considering that polymers like chitin contain amino groups that react with genipin in a moderate reaction, all reactions were performed for 24 hours at RT and 37° C. It seems that the extent of the crosslinking was affected by key factors such as genipin concentration (10 mM, 20 mM) and reaction temperature (RT, 37° C.), where crosslinked membranes prepared at 37° C. in both genipin concentrations could have a higher degree of crosslinking.

Figure 12:
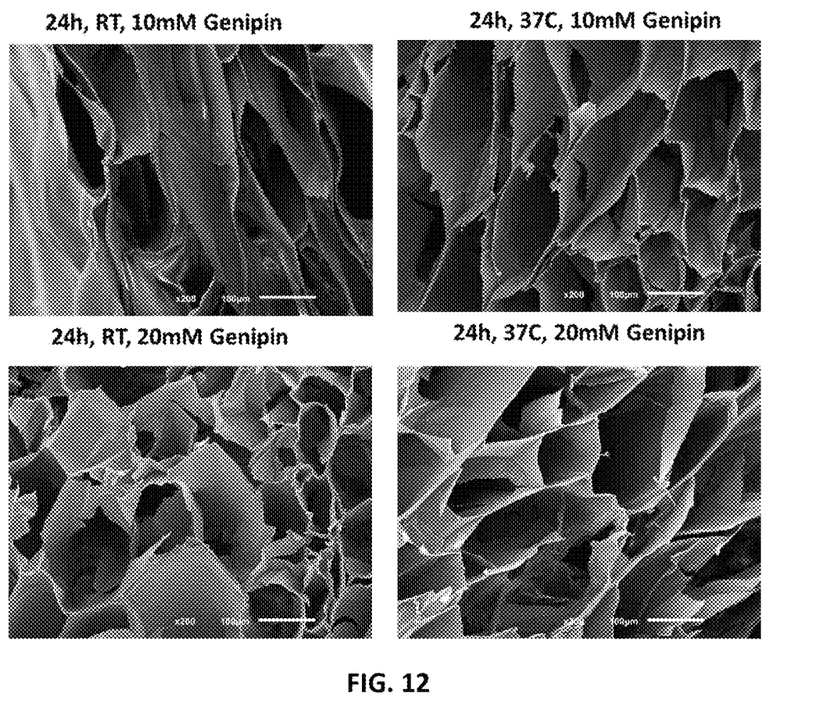
FIG. 12. SEM images of the crosslinked chitin and SAIB/chitin based membranes.

In an embodiment, the SEM images of the cross-sections of the membranes (FIG. 12) showed that they have a porous formation that could be interesting for tissue engineering applications. Therefore, it is reasonable to assume that genipin may serve as a crosslinker to produce porous crosslinked chitin and SAIB/chitin membranes. The present disclosure relates to an innovative technology by green processing SAIB. The produced 3D scaffolds were physicochemical and biologically characterized. By taking advantage of the properties of the used ionic liquid ([BMIM][Ac]) it was possible to achieve a good dissolution of SAIB, chitin and silk fibroin. It was possible to efficiently remove the ionic liquid. The presence of Chitin, Silk fibroin and SAIB is easily detected in the FTIR spectra obtained. Moreover, the aerogel morphology was possible to obtain in certain conditions. Furthermore, SAIB contributed to decrease the crystallinity of the scaffolds. It was found that in the biological outcomes of the SAIB/chitin scaffolds demonstrated herein reveals a positive effect of the structures over cell adhesion and proliferation.

These results clearly show the potential of the used approach. The shown characteristics prove the applicability of the products in skin and cartilage repair.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

REFERENCES

1. Reynolds R C. Metabolism and pharmacokinetics of sucrose acetate isobutyrate (SAIB) and sucrose octaisobutyrate (SOIB) in rats, dogs, monkeys or humans: a review.

Food and Chemical Toxicology. 1998; 36(2):95-9. doi: 10.1016/s0278-6915(97)00123-3.
2. Cheng T, Valtchev P, Murphy C, Cantrill L, Dehghani F, Little D et al. A sugar-based phase-transitioning delivery system for bone tissue engineering. Eur Cell Mater. 2013; 26:208-21.
3. FDA U. Part 172-Food additives permitted for direct addition to food for human consumption. § 172.898-Bakers yeast glycan. Code of Federal Regulations (CFR) Title. 2006:119.
4. Silva S D S, Mano J, Reis R L. Ionic liquids in the processing and chemical modification of chitin and chitosan for biomedical applications. Green Chemistry. 2016.
5. Al Sagheer F, Al-Sughayer M, Muslim S, Elsabee M Z. Extraction and characterization of chitin and chitosan from marine sources in Arabian Gulf. Carbohydrate Polymers. 2009; 77(2):410-9.

The invention claimed is:

1. A composite for the release of a bioactive substance, wherein the composite comprises a composition comprising:
   sucrose acetate isobutyrate dissolved in an ionic liquid; and
   an additive selected from group consisting of chitin, silk fibroin, cellulose, alginate, chitosan, gellan gum, dextrin, collagen, guar gum, carrageenan, heparin, kefiran, and mixtures thereof, wherein the composite is a gel, a membrane or a scaffold, and wherein the scaffold has a pore size of 0.5-50 μm.

2. The composite of claim 1, wherein the composition comprises:
   10-60% (w/V) of sucrose acetate isobutyrate; and
   40-90% (w/V) of the additive.

3. The composite of claim 1, wherein the composition comprises 30-50% (w/V) of sucrose acetate isobutyrate.

4. The composite of claim 1, wherein the composition comprises 55-65% (w/V) of the additive.

5. The composite of claim 1, wherein the additive is dissolved in the ionic liquid.

6. The composite of claim 1, wherein the ionic liquid is selected from the group consisting of: 1-butyl-3-methylimidazolium chloride, 1-butyl-3-methyl imidazolium acetate, 1-allyl-3-methylimidazolium bromide, 1-ethyl-3-methylimidazolium dimethyl phosphate, 1-carboxymethyl-3-methylimidazolium hydrochloride, 1-ethyl-3-methylimidazolium chloride, 1-ethyl-3-methylimidazolium acetate, and mixtures thereof.

7. The composite of claim 1, further comprising a ceramic additive, wherein the ceramic additive is selected from hydroxyapatite, bioglass, silicon substituted hydroxyapatite (HAp), tri-calcium phosphate (TCP), or combinations thereof.

8. The composite of claim 7, wherein the release of the bioactive substance is a sustained release and the sustained release is 1-2 months, wherein the bioactive substance is selected from the group consisting of: antibiotic, growth factor, nanoparticles and micro-particles, and mixtures thereof, and wherein the nanoparticles are dendrimers nanoparticles and the micro-particles are systems of synthetic polymers selected from the group consisting of: poly(lactic-co-glycolic acid) (PLGA), poly(lactic acid) (PLA), natural polymers, and mixtures thereof.

9. The composite of claim 8, wherein the antibiotic is bacitracin, erythromycin, polymyxin, vancomycin, gentamycin, kanamycin, neomycin, amoxicillin streptomycin, rapamycin, streptomycin, polymyxin, colistin, tyrocidine, gramicidin, cyclosporin, or mixtures thereof.

10. The composite of claim 8, wherein the growth factor is an epidermal growth factor, platelet-derived growth factor, growth hormone releasing factor, platelet derived growth factor, nerve growth factor, or mixtures thereof.

11. The composite of claim 8, wherein the dendrimers nanoparticles are polyamidoamine (PAMAM).

12. The composite of claim 1, wherein the composite is suitable for treating or preventing bone disease or defect, cartilage disease or defect, cornea disease or defect, skin disease or defect, vascular tissue disease or defect, peripheral nerve disease or defect, spinal cord disease or defect, brain diseases or defect or wound healing.

* * * * *